United States Patent [19]

Nabih

[11] 3,948,920
[45] Apr. 6, 1976

[54] NEW ANTI-MALARIAL AGENTS
[75] Inventor: Ibrahim Mohamed Nabih, Cairo, Egypt
[73] Assignee: Aktiebolaget Astra, Sodertalje, Sweden
[22] Filed: Aug. 7, 1974
[21] Appl. No.: 495,270

Related U.S. Application Data
[62] Division of Ser. No. 296,877, Oct. 12, 1972, abandoned.

[30] Foreign Application Priority Data
Oct. 19, 1971 Sweden............................. 13236/71

[52] U.S. Cl...... 260/288 A; 260/279 A; 260/279 R; 260/287 AR; 260/288 CE; 260/288 R; 424/257; 424/258
[51] Int. Cl.$^2$..................................... C07D 215/44
[58] Field of Search....... 260/288 R, 288 CE, 288 A

[56] References Cited
UNITED STATES PATENTS
2,474,821  7/1949  Burckhalter.................... 260/288 A
3,075,981  1/1963  Surrey.......................... 260/288 A OTHER PUBLICATIONS
Nabih; Experientia, Vol. 27, p. 1114 (1972).

Primary Examiner—Raymond V. Rush
Assistant Examiner—Mary C. Vaughn
Attorney, Agent, or Firm—Brumbaugh, Graves, Donohue & Raymond

[57] ABSTRACT
Compounds of the formula wherein A designates that the fused six-membered ring could be either unreduced, partially reduced or totally reduced and wherein $R^1$ is $-N(CH_3)_2$, $-N(C_2H_5)_2$, or $-N(CH_2CH_2Cl)_2$ and $R^2$ is and R is an acyl group with 1–5 carbon atoms, and pharmaceutically acceptable salts thereof; processes for their preparation; pharmaceutical preparations containing at least one of these compounds and the use thereof in the treatment of and protection against malaria infection.

3 Claims, No Drawings

ANTI-MALARIAL AGENTS

This is a division of application Ser. No. 296,877, filed Oct. 12, 1972, now abandoned.

Over one billion people now live in areas where malaria has been eradicated or where eradication is under way. Global eradication is a long way off, however, as most of the remaining population of the earth resides in areas where malaria is still endemic or epidemic. Complete protection of areas free from malaria will require eventual elimination of the disease everywhere. The economic losses due to malaria are enormous. Few infections of man have had such an impact on the lifes and fortunes of people. Malaria had been considered to one of the most widespread human diseases. It was estimated that it effects more than 200 million people thus causing two million deaths each year. The resistance of the strain *Plasmodium falciparum* to usually effective doses of most synthetic anti-malarial drugs has increased in South-America and Southeast-Asia. This is a serious problem and forms a potential threat in these areas.

Drugs of the aminoquinoline type have been known for their activity against the erythrolytic stages of the malaria parasite in humans. Of these, the mostly used are Chloroquine (I) and Amodiaquine (II)

Thus development of new agents that would structurally include systems related to naphthoquinones besides the nitrogen heterocyclic ones might be useful as new antimalarial agents. Since the resistance of parasite to nitrogen heterocyclics should not imply resistance to compounds of the quinoid type as both are acting through different mechanisms. These considerations suggested synthesis of naphtolic compounds of the general formula

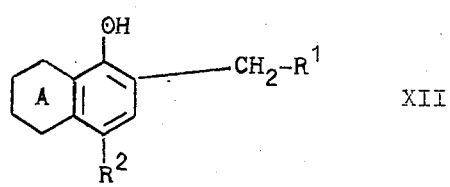

wherein A designates that the fused six-membered ring could be either unreduced, partially reduced or totally reduced and wherein $R^1$ is $-N(CH_3)_2$, $-N(C_2H_5)_2$,

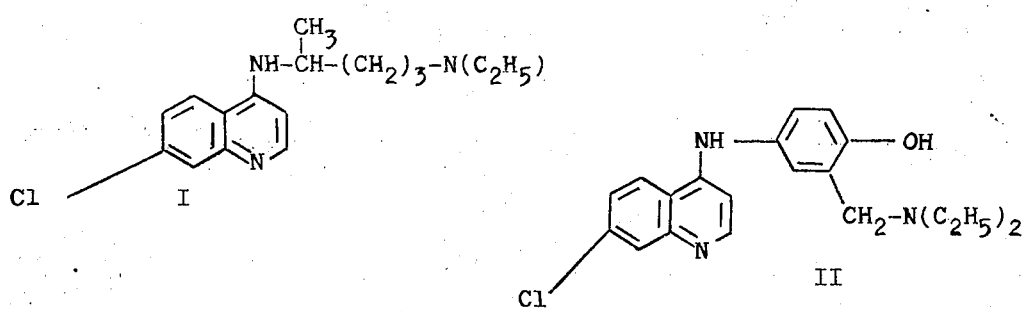

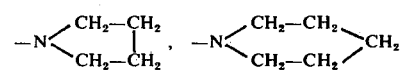

or $-N(CH_2CH_2Cl)_2$, and $R^2$ is

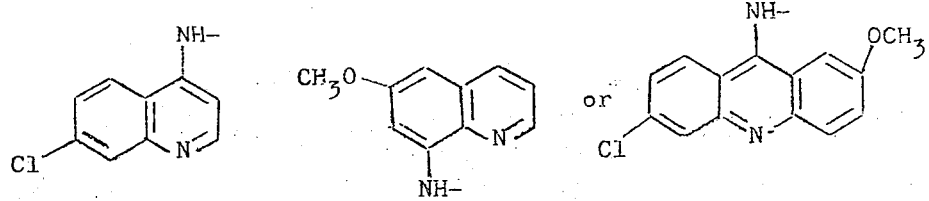

of 2-alkyl-3-hydroxy-1,4-naphtoquinone derivatives that apparently act by inhibiting the respiration of plasmodia. Generally, the naphthoquinone antimalarials are powerful inhibitors to respiratory system in the parasite.

The non-toxic salts of the compounds of the present invention include also their salts of acids such as hydrochloric, sulphuric, phosphoric and oxalic acids.

The specially preferred compounds of the invention are:

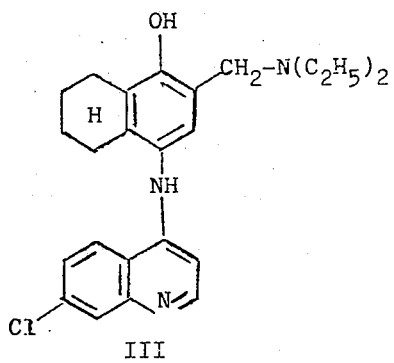
III
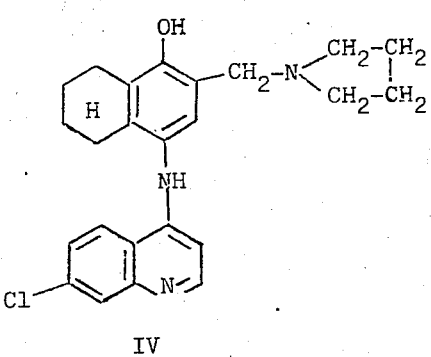
IV
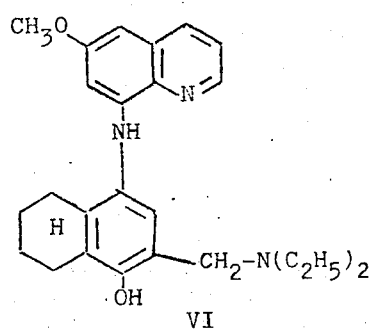
VI
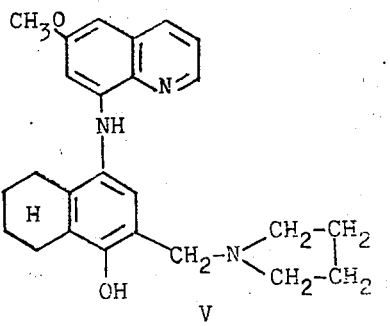
V
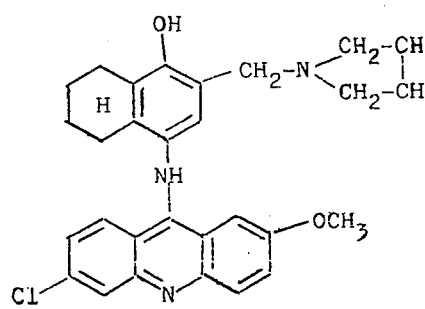
VIII
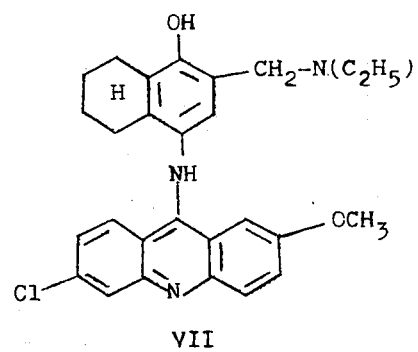
VII
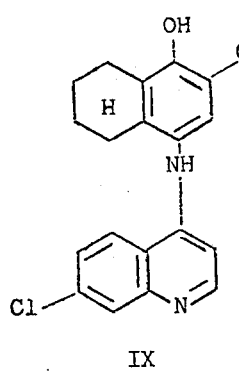
IX
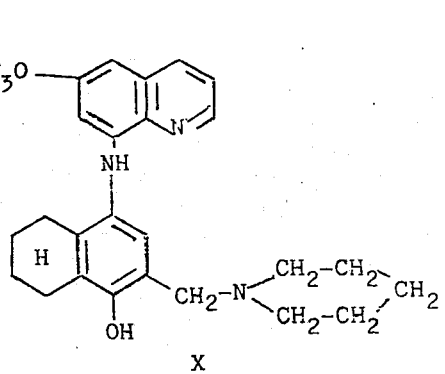
X
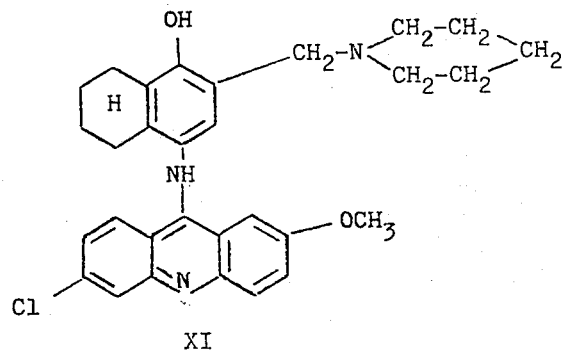
XI The presence of the piperidine rest in compounds IX, X and XI, in order to benefit from the steric hinderance induced about the piperidine nitrogen atom which may add the advantage of longer activity for the included compounds.

The naphtholic part in these structures, the reduced ring as 5, 6, 7, 8-tetrahydro-I-naphthol could be totally reduced as it is or partially in the dihydro-form or unreduced in the aromatic form. Examples where the naphtholic part is unreduced are compounds:

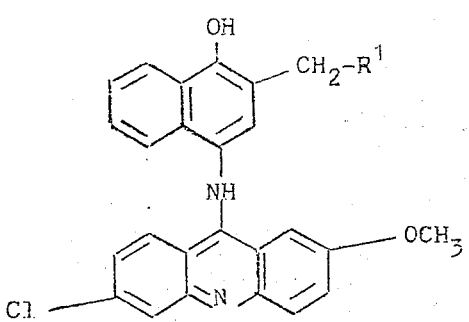

wherein $R^1$ has the meaning given above.

The following examples will further illustrate the invention:

EXAMPLE 1 a.
2-Diethylaminomethyl-4-acetamino-5,6,7,8-tetrahydro-I-naphthol

Preparation of starting material for preparation of compound III. A mixture of 9,4 g (0.05) mole of 4-acetamino-5,6,7,8-tetrahydro-I-naphthol, 4 g diethyle amine and 1.6 g of paraformaldehyde in 200 ml absolute alcohol was refluxed for 12 h. After cooling the reaction mixture was filtered and the filtrate diluted with water. The formed precipitate was collected. After recrystallization from alcohol, it melted at 157°–159°C and gave 10.8 g.

Analysis. Calculated for $C_{17}H_{26}N_2O_2$: C, 70.80, H 8.96, N 10.21. Found: C 71.02, H 9.05, N 10.20.

b.
4-(7-Chloro-4-quinolylamino)-2-diethylaminomethyl-5, 6, 7, 8-tetrahydro-I-naphthol (III)

A solution of 2 g of 2-diethylaminomethyl-4-acetamino-5,6,7,8-tetrahydro-I-naphthol, and 50 ml of concentrated hydrochloric acid in 200 ml of absolute ethanol was refluxed for 12 hours. Thereafter the solvent was distilled and the residue treated with ammonium hydroxide then extracted with ether. The etherial extract was washed with water and dried over magnesium sulphate. Then the ether was distilled to reside the amine. From this residual amine 6 g was mixed with 4 g of 4-dihchloroquinoline and few drops of conc. HCl in 50 ml of absolute ethanol and refluxed for 12 hours. Thereafter, the reaction mixture was cooled and diluted with water to double its volume then poured over a cold solution of ammonia. The formed precipitate was collected and washed with water. After drying, it weighed 9.2 g (90 % yield) of 4-(7-chloro-4-quinolylamino)-2-diethylaminomethyl-5,6,7,8-tetrahydro-I-naphthol (III). After recrystallization, it melted at 215°–217°C.

Analysis: Calculated for $C_{24}H_{28}N_3O$ Cl: C 70.32, H 6.83, N 10.27, Cl 8.66. Found: C 70.28, H 7.12, N 10.16, Cl 8.55.

EXAMPLE 2

However the same compound III can be obtained through an alternative route as follows:

A mixture of 6.5 g (0.04) mole of 4-amino-5,6,7,8-tetrahydro-I-naphthol, 7.8 g (0.04) mole of 4.7-dichloroquinoline and 4 ml of conc. HCl was refluxed

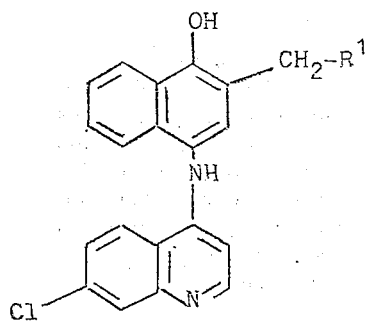

for 4 hours. After cooling the formed 4-(7-chloro-4-quinolyl) 5,6,7,8-tetrahydro-I-naphtholhydrochloride was collected. After recrystallization from ethanol, it melted over 300° with dec. and weighed 12 g.

Analysis: Calculated for $C_{19}H_{18}N_2O$ Cl HCl: C 62.45, H 5.02, N 7.76, Cl 19.64. Found: C 62.44, H 5.01, N 7.64, Cl 19.58.

From this hydrochloride 7.2 g was mixed with 2.4 ml of diethylamine and 1.6 ml formaline(37 %), then refluxed for 4 hours; the formed white precipitate was warmed with ammonia solution, filtered, washed with water and dried. After recrystallization, it gave 7.5 g of III, m.p. 215°–217°C, identical to the that prepared by the former method, namely through the condensation of 4,7-dichloroquinoline and diethylaminomethyl-4-amino-5,6,7,8-tetrahydro-I-naphthol (with no depression in admixed melting point).

EXAMPLE 3

Preparation of 4-(6-chloro-2-methoxy-9-acridyl-amino)-2-diethylaminomethyl-5,6,7,8-tetrahydro-I-naphthol (VII)hydrochloride A mixture of 9.6 g of 2-diethylaminomethyl-4-amino-5,6,7,8-tetrahydro-I-naphthol, 8.4 g of 6.9 dichloro-2-methoxy acridine in 600 ml absolute ethanol and few drops of conc. HCl was refluxed for 12 hours. After cooling a yellow precipitate formed that was collected and recrystallized from ethanol to give 13.2 g it melted over 300°C with dec.

Analysis: Calculated for $C_{29}H_{32}N_3O_2Cl$ HCl $H_2O$: C 64.01, H 6.49, N 7.72, Cl 13.03. Found: C 64.01, H 6.42, N 7.68, Cl 13.07.

EXAMPLE 4 a.
2-piperidinomethyl-4-acetamino-5,6,7,8-tetrahydro-I-naphthol

Preparation of intermediate for preparing compound IV, 4-(7-chloro-4-quinolylamino)-2-N-piperidinomethyl-5,6,7,8-tetrahydro-I-naphthol. A mixture of 9 g of 4-acetamino-5,6,7,8-tetrahydro-I-naphthol, 4 ml of formaline solution (37 %) in 150 ml absolute alcohol was refluxed for 8 hours. After cooling, this was poured over cold water. The formed white precipitate was collected and dried to give 16.6 g of 2-piperidinomethyl-4-acetamino-5,6,7,8-tetrahydro-I-naphthol. After recrystallization from ethanol, it melted at 166°–167°C.

Analysis: Calculated for $C_{18}H_{20}O_2N_2$: C 71.51, H 8.69. N 9.27. Found: C 71.48, H 8.74, N 8.98.

b.
4-(7-chloro-4-quinolylamino)-2-N,piperidinomethyl-5,6,7,8-tetrahydro-I-naphthol (IV)

A mixture of 9.8 g of 4,7-dichloroquinoline and 13 g of 2-piperidino-methyl-4-amino-5,6,7,8-tetrahydro-I-naphthol (this is obtained through the acid hydrolysis of the acetamino-derivative described above), in 200 ml of absolute ethanol and a few drops of conc. HCl was refluxed for 12 hours, thereafter the solvent was distilled over and the residue washed with ether and recrystallized from aqueous methanol to give 8.9 g of IV as hydrochloride, m.p. 233°C (dec).

Analysis: Calculated for $C_{25}H_{28}N_3O$ Cl HCl $H_2O$: N 8.83, Cl 14.91. Found: N 8.84, Cl 14.92.

EXAMPLE 5

Preparation of
4-(6-chloro-2-methoxy-9-acridylamino9--acridylamino)--piperidinomethyl-5,6,7,8-tetrahydro-I-naphthol (VIII)

A mixture of 2.6 g of 2,N-piperidinomethyl-4-amino-5,6,7,8-tetrahydro-I-naphthol (obtained as above described), 2.8 g 6.9-dichloro-2-methoxyacridine in 40 ml of absolute ethanol and a few drops of conc. HCl was refluxed for 12 hours, after cooling the formed yellow precipitate was collected and recrystallized from ethanol to give 2.5 g of the product as hydrochloride, m.p. over 300°C.

Analysis: Calculated for $C_{30}H_{32}N_3O_2$ Cl HCl $H_2O$: C 64.81, H 6.32, N 7.56, Cl 12.75. Found: C 64.80, H 6.35, N 7.49, Cl 12.75.

EXAMPLE 6 a. 2-diethylaminomethyl-4-nitro-I-naphthol

Preparation of intermediate 4-(7-chloro-4-quinolylamino)-2-diethylaminomethyl-I-naphthol. A mixture of 2.4 g of 4-nitro-I-naphthol and 3 ml of diethylamine in 50 ml of absolute alcohol was thoroughly shaken. To this was added 4.8 ml of formaline solution (37 %) under shaking. The yellow formed precipitate was collected and recrystallized from ethanol to give 13.2 g of the product as orange crystals of m.p. 158°–160°C.

Analysis: Calculated for $C_{15}H_{18}N_2O_3$: C 65.67, H 6.62, N 10.22. Found: C 65.64, H 6.54, N 10.19.

b.
4-(7-chloro-4-quinolylamino)-2-diethylaminomethyl-I-naphthol (XII)

A mixture of 13.8 g of diethylaminomethyl-4-amino-I-naphthol (obtained through the catalytic reduction of the above described nitro-compound), 9.9 g of 4,7-dichloroquinoline in 500 ml of absolute ethanol and 10 ml of conc. HCl acid was refluxed fro 10 hours. After cooling the mixture was treated with sodium carbonate solution (10 %). The formed precipitate was collected and dried to give 14.5 g of the product. It was identified as its picrate, that was recrystallized from acetone and melted at 235°–237°C.

Analysis: Calculated for $C_{30}H_{27}N_6O_8Cl$: C 56.72, H 4.25, N 13.24. Found: C 56.68, H 4.28, N 13.36.

Biological Testing

Groups of mice of average weight of 20-22 g already infected with *Plasmodium berghei* were given subcutaneously, after 3 days of infection, doses of 25, 10, 5 mg/kg body weight from the compound III suspended or partially dissoluted in water or sesame oil. These doses in the different groups were given daily for 4 consecutive days. All the treated groups with the different mentioned doses up to the level 5 mg/kg body weight were cured from the infection. No parasitaemie could be detected in the treated groups, after contineous blood examination for 6 weeks. While the control groups, that were untreated, showed with parallel examination of their blood heavy infection, and death occured in the control, the untreated within 7–9 days. Also, compound III showed curative effect when orally given. Besides, compound III possesses remarkable depot-effect. When it was subcutaneously given twice to groups of mice in doses of 100 mg/kg body weight and these groups were inoculated with parasitized cells, submitted to heavy infection, no parasitaemie could be detected in spite of the heavy infection or the massive infection. Compared with the control groups that were untreated with compound III, the infection was heavily developed in the controls. This means, that compound III possesses CURATIVE and PROPHYLACTIC effect against malaria infection.

The compound XII could be O-acylated in manners known to art to give compounds of the structure

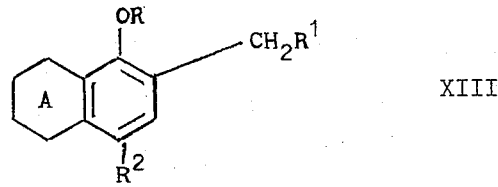

XIII wherein R is an acyl group with 1-5 carbon atoms, such as acetyl and A, $R^1$ and $R^2$ have the meaning given above.

The compound XIII could also be prepared using O-acetylated starting materials.

I claim:
1. A compound selected from the group consisting of a compound of the formula

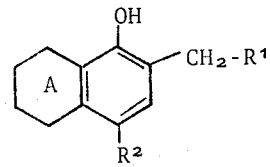

wherein A designates that the fused six-membered ring could be either unreduced, partially reduced, or totally reduced, and wherein $R^1$ is $-N(CH_3)_2$, $-N(C_2H_5)_2$,

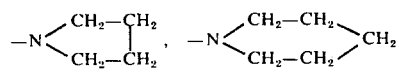

or $-N(CH_2CH_2Cl)_2$ and $R^2$ is and pharmaceutically acceptable salts thereof.
2. The compound
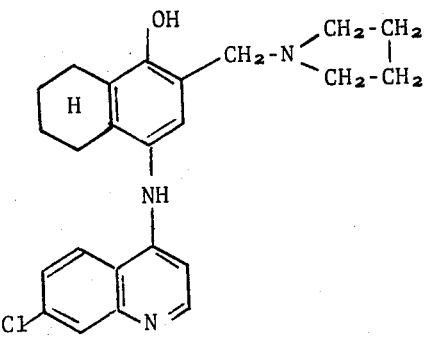
or pharmaceutically acceptable salts thereof.
3. The compound
or pharmaceutically acceptable salts thereof.
* * * * *